United States Patent
Kannan et al.

(10) Patent No.: US 9,488,618 B2
(45) Date of Patent: Nov. 8, 2016

(54) GENERATOR RETAINING RING AND OTHER COMPONENT THERMAL DEGRADATION EVALUATION BY EDDY CURRENT NON-DESTRUCTIVE EXAMINATION

(71) Applicant: SIEMENS ENERGY, INC., Orlando, FL (US)

(72) Inventors: Kalyan Kannan, Oviedo, FL (US); Kevin P. Bailey, Chuluota, FL (US); Neil L. Kilpatrick, Winter Springs, FL (US)

(73) Assignee: Siemens Energy, Inc., Orlando, FL (US)

( * ) Notice: Subject to any disclaimer, the term of this patent is extended or adjusted under 35 U.S.C. 154(b) by 368 days.

(21) Appl. No.: 14/071,707

(22) Filed: Nov. 5, 2013

(65) Prior Publication Data
US 2015/0123512 A1    May 7, 2015

(51) Int. Cl.
*B65D 5/50*    (2006.01)
*H02N 2/00*    (2006.01)
*G01B 17/02*   (2006.01)
*G01N 27/90*   (2006.01)
*H02K 15/00*   (2006.01)

(52) U.S. Cl.
CPC .............. *G01N 27/90* (2013.01); *H02K 15/00* (2013.01)

(58) Field of Classification Search
CPC ....... H02K 11/00; G01N 27/90; G01N 29/10
USPC .................. 310/273, 336; 73/866.5; 324/220
See application file for complete search history.

(56) References Cited

U.S. PATENT DOCUMENTS

| | | | | |
|---|---|---|---|---|
| 4,970,670 | A | * | 11/1990 | Twerdochlib .................... 702/99 |
| 4,982,158 | A | * | 1/1991 | Nakata et al. ................. 505/162 |
| 4,989,406 | A | | 2/1991 | Vdoviak et al. |
| 5,334,934 | A | | 8/1994 | Viertl |
| 6,941,639 | B2 | | 9/2005 | Zhang et al. |
| 2004/0108019 | A1 | * | 6/2004 | Schnell et al. ................ 148/509 |

FOREIGN PATENT DOCUMENTS

| | | |
|---|---|---|
| EP | 1426760 A1 * | 6/2004 |
| GB | 2263777 A1 * | 8/1993 |

OTHER PUBLICATIONS

GE Energy "title: Generator In-Situ Inspections", GER-3954C, Mar. 2012.*
Markman et al., "Generator In-Situ Inspections, A Critical Part of Generator Maintenance Cost Reduction; GER-3954C", Mar. 2012, pp. 1-16; GE Energy, Schenectady, NY USA.

* cited by examiner

*Primary Examiner* — Jose Gonzalez Quinones

(57) ABSTRACT

Eddy current non-destructive examination and evaluation of physical properties of a component, such as a generator retaining ring, after experiencing potentially degrading thermal exposure during any stage of manufacture, assembly and service use, is performed to determine whether it is acceptable for service use, requires further modification (e.g., additional heat treatment processing) or whether is permanently unsuitable for service. Eddy current test measurements are correlated with component temperature exposure (e.g., absolute temperature and/or cumulative time-temperature heat absorption) and cumulative alteration of the component physical properties, such as, among others, material yield strength (YS), toughness, and tensile ductility. Using the eddy current test measurements and reference data correlating electrical conductivity with ring material thermal exposure, the component's physical properties are evaluated to determine its serviceability. The testing can be performed in situ in the field, such as for evaluation of generator rings within field serviced generators.

13 Claims, 3 Drawing Sheets

GENERATOR RETAINING RING AND OTHER COMPONENT THERMAL DEGRADATION EVALUATION BY EDDY CURRENT NON-DESTRUCTIVE EXAMINATION

BACKGROUND OF THE INVENTION

1. Field of the Invention

The invention relates to eddy current non-destructive examination (NDE) and evaluation of physical properties of a component, such as a generator retaining ring, rotor forging, rotor wedge, damper bar or other generator component, after experiencing potentially degrading thermal exposure during any stage of manufacture, assembly and service use. In this invention eddy current test measurements are correlated with component thermal exposure (e.g., absolute temperature and/or cumulative time-temperature heat absorption) and cumulative alteration of the component physical properties, such as, among others, material yield strength (YS), toughness, and tensile ductility. In this invention, using the eddy current test measurements and reference data correlating electrical conductivity with ring material thermal exposure, the component's physical properties are evaluated to determine whether it is acceptable for service use, requires further modification (e.g., additional heat treatment processing) or whether is permanently unsuitable for service. The invention test method can be employed with in situ components, such as generator rings within field serviced generators, without altering the component structure.

2. Description of the Prior Art

FIGS. 1 and 2 show a known generator 20, having a generator rotor 22 with rotor windings, including end turn bends 24. A slip layer liner 26 covers the end turn bends 24 and one or more locking keys 28 project radially from the rotor circumference. Electrical generator retaining rings 30 at each axial end of the rotor 22 support the rotor winding end turns 24 against centrifugal force generated by rotor cyclic rotation, and thus are subjected to annularly oriented stress. Thus the retaining rings 30 are designed to be tolerant to high stress levels while possessing adequate low cycle fatigue and toughness. The retaining rings 30 are generally constructed of non-magnetic material, in order to minimize rotor end leakage flux, which also reduces rotor operating temperature. Exemplary known materials used to construct the generator retaining rings 30 include 8Mn-8Cr-4Ni austenitic steel, 9Mn-6Cr-4Ni austenitic steel and 18Mn-5Cr austenitic steel. In recent decades 18Mn-18Cr austenitic steel has become commonly used due to its higher corrosion resistance and lessened likelihood of stress corrosion cracking while the generator 20 is in service.

Generally, the retaining rings 30 are shrink-fitted (by application of heat to expand the rings and subsequent shrinkage after cooling) onto the end of the generator rotor 22 body, with an interior annular surface formed ring groove 32 interlocking with generator body locking key(s) 28. This axial interlocking, prevents ring 30 separation from the generator rotor body 22 as the rotor windings and their end turns 24 expand in the axial direction as they are internally heated by the electromagnetic forces generated within the generator 20. The resultant shrink fit also creates an additional mechanical stress within the retaining rings 30, which is anticipated and compensated for in the ring design parameters. However, thermal degradation of the retaining ring 30 structure physical properties during shrink fit heating and service operational heating is more difficult to anticipate and compensate for in the ring design. It is even more challenging to determine the extent of thermal degradation impact on previously in-service retaining rings 30 and other generator structures physical properties when a generator 20 is periodically inspected serviced after many hours of field operation.

Retaining ring 30 material physical properties, such as such as, among others, material yield strength (YS), toughness, and tensile ductility change are altered by thermal exposure; whether absolute temperature exposure or time-temperature exposure. Generator retaining ring 30 adverse thermal exposures due to accidental overheating in shrink fit assembly or service can result in significant loss of its material physical properties. There exist critical absolute temperature and cumulative time exposure limits above which such thermal exposure can adversely impact generator ring 30 performance. However, there is no reliable and quantitative non-destructive method to evaluate the level of overheating and determine if such deleterious thermal exposure has occurred.

In the past, engineers have relied on "temper colors" or surface tints to estimate temperature of exposure. This is not very reliable, as it is quite subjective and also depends on other variables such as initial surface condition, exposure time and environment. Microstructural evaluation by in-situ metallography is presently used but is time-consuming and often generates ambiguous test results. In the absence of reliable and repeatable evaluation of generator retaining ring 30 thermal exposure, manufacturers and users tend to scrap retaining rings 30 or other generator structures that are suspected of any degree of overheating, rather than risk future potential deleterious field service. Scrapping generator components and replacing with new rings entails significant cost and time delays.

Known NDE of an industrial object by an eddy current modality identifies discontinuities, such as cracks or voids, by passage of a steady state alternating current or pulsed current waveform in a test probe transmitter coil that is electromagnetically coupled in close proximity to an electrically conductive test object. The changing current flow in the probe transmitter generates a changing transmitted magnetic field waveform that in turn induces a generated eddy current in the electromagnetically coupled test object. Variations in the phase and magnitude of these generated eddy currents within the test object create a responsive or reflected magnetic field waveform that is in turn sensed by a test probe receiver coil as an induced received or reflected current flow. In some known eddy current NDE systems the test probe's transmitter coil also functions as the receiver coil. Thus, variations in the electrical conductivity or magnetic permeability of the test object, or the presence of any flaws, will cause a change in eddy current and a corresponding change in the phase and amplitude of the reflected magnetic waveform as sensed by the test probe receiver changes in its current waveform. Amplitude and intensity of an eddy current within a test object will stay substantially constant if its magnetic transmission characteristics (which impact the reflected waveform) are substantially constant. Anomalies in the test object alter its magnetic transmission characteristics at the anomaly location. Accordingly, anomalies and their spatial location within the test object can be detected by determining if the magnetic transmission characteristics of the material being scanned are consistent with the presence or absence of an anomaly at each scan spatial location. However, a thermally degraded test component may not have any internal flaws that can be detected by known eddy current NDE methods.

Thus, a need exists for a non-destructive examination (NDE) and evaluation of the physical properties of components, such as generator retaining rings or other generator components, after they experience potentially degrading thermal exposure during any stage of manufacture, assembly and service use.

A separate additional need exists for in situ non-destructive examination (NDE) and evaluation of the physical properties of components, such as generator retaining rings or other generator components, after they experience potentially degrading thermal exposure, so that the component does not need to be separated from its operative environment.

SUMMARY OF THE INVENTION

Accordingly, an object of the invention is to create a method for non-destructive examination (NDE) and evaluation of the physical properties of components, such as generator retaining rings, rotor forgings, stainless wedges, damper bars or other generator components, after they experience potentially degrading thermal exposure during any stage of manufacture, assembly and service use. In this manner degraded components are identified and replaced without wasting additional service or manufacturing expense, but serviceable components are not unnecessarily scrapped.

Another separate object of the invention is to create a method for in situ non-destructive examination (NDE) and evaluation of the physical properties of components, such as generator retaining rings or other generator components, after they experience potentially degrading thermal exposure, so that the component does not need to be separated from its operative environment. In the example of generator retaining rings, such a needed NDE evaluation method would facilitate thermal degradation evaluation of rings after assembly shrink fit or field service inspection of rings within a generator at a power plant to determine whether the generator rotor needs refurbishment.

Electrical conductivity measurements made on the surface of components, such as generator rings, is an indicator of the thermal exposure experienced by the ring. More specifically, electrical conductivity measurements, made using a known eddy current based probe and measurement system, are indicative of and are correlated with changes in component physical properties that are attributable to the thermal exposure. It is believed that thermal exposure influences development of an oxide layer on a component external surface. That oxide layer impacts surface eddy current conductivity. Thus, measured eddy current readings can be correlated with thermal exposure. By referencing data correlating electrical conductivity and ring thermal exposure the component's physical properties can be evaluated. Based on the evaluation the measured component can be classified as acceptable or not acceptable for use.

For example, reference data can be compiled by heating a component constructed of a given material to a designated temperature over a desired time exposure and its thermal conductivity subsequently measured by eddy current testing. The component's physical properties at any given thermal exposure temperature/exposure time are independently evaluated by known destructive or non-destructive methods. By repeating plural component conductivity and physical properties tests of the same material at different time/temperature thermal exposures a reference data base can be compiled. Design parameters and use decisions can be based on acceptable component material physical properties, which are correlated to thermal exposure. With the present invention test methods the eddy current measurements are correlated with thermal exposure.

After compilation of thermal exposure/eddy current/physical properties reference data subsequent eddy current inspection readings on other different components constructed of the same material can be compared to the reference data. Based on that comparison the component's serviceability can be evaluated. Component NDE eddy current readings can be taken during any stage of manufacture, assembly and service use, even while the component is in situ within an apparatus. In the example of generator retaining rings, such a needed NDE evaluation method would facilitate thermal degradation evaluation of rings after assembly shrink fit or field service inspection of rings within a generator at a power plant to determine whether the generator rotor needs refurbishment. With the NDE test methods of the present invention eddy current readings are used to identify degraded components in need of replacement without wasting additional service or manufacturing expense, but serviceable components are not unnecessarily scrapped.

The eddy current/thermal exposure correlation testing method of the invention is non-destructive and does not require any disturbance to the component heat-treated surface by surface grinding, scraping off oxide scale, etc.). No extra material needs to be removed from the generator ring or other component to verify base material physical properties. Thus there is no need to alter, destroy or otherwise modify the ring in the process of assessing its acceptability for future service.

The present invention NDE and evaluation method is also quantitative, with measured data in the form of electrical conductivity values, instead of relying on qualitative and ambiguous measures such as temper colors or surface tint. The required test equipment is a known eddy current hand-held tool that can be used anywhere, whether at a generator manufacturing facility, a service repair center or in the field at power plant site. On site evaluation eliminates the need to transport generators or other tested equipment to a remote test center. By conducting an onsite test, an on-the-spot immediate decision can be made whether the tested component that may have been suspected of having suffered adverse thermal exposure can continue in service or whether remedial repairs are necessary.

Exemplary embodiments of the invention feature a method for non-destructive evaluation of physical properties of material forming a component that are attributable to thermal exposure, by measuring component's electrical conductivity with an eddy current test system. The component's measured electrical conductivity is compared to reference data correlating electrical conductivity with ring material thermal exposure. The component thermal exposure is determined based on the measured electrical conductivity and the reference data. The component's physical properties are evaluated for acceptability for use based at least in part on the determined thermal exposure. The component may comprise a generator retaining ring, rotor forging, rotor wedge, damper bar or other generator component. The component may be constructed of austenic steel, such as 8Mn-8Cr-4Ni austenitic steel, 9Mn-6Cr-4Ni austenitic steel, 18Mn-5Cr austenitic steel or 18Mn-18Cr austenic steel.

Other exemplary embodiments of the invention feature a method for non-destructive evaluation of physical properties of material forming a generator retaining ring that are attributable to thermal exposure, by measuring the generator ring's electrical conductivity with an eddy current test system. The generator ring's measured electrical conductivity is compared to reference data correlating electrical conductivity with ring material thermal exposure. The ring thermal exposure is determined based on the measured electrical conductivity and the reference data. The generator ring physical properties are evaluated for acceptability for use in a generator based at least in part on the determined thermal exposure.

The objects and features of the present invention may be applied jointly or severally in any combination or sub-combination by those skilled in the art.

BRIEF DESCRIPTION OF THE DRAWINGS

The teachings of the present invention can be readily understood by considering the following detailed description in conjunction with the accompanying drawings, in which.

To facilitate understanding, identical reference numerals have been used, where possible, to designate identical elements that are common to the figures.

DETAILED DESCRIPTION

Figure 1:
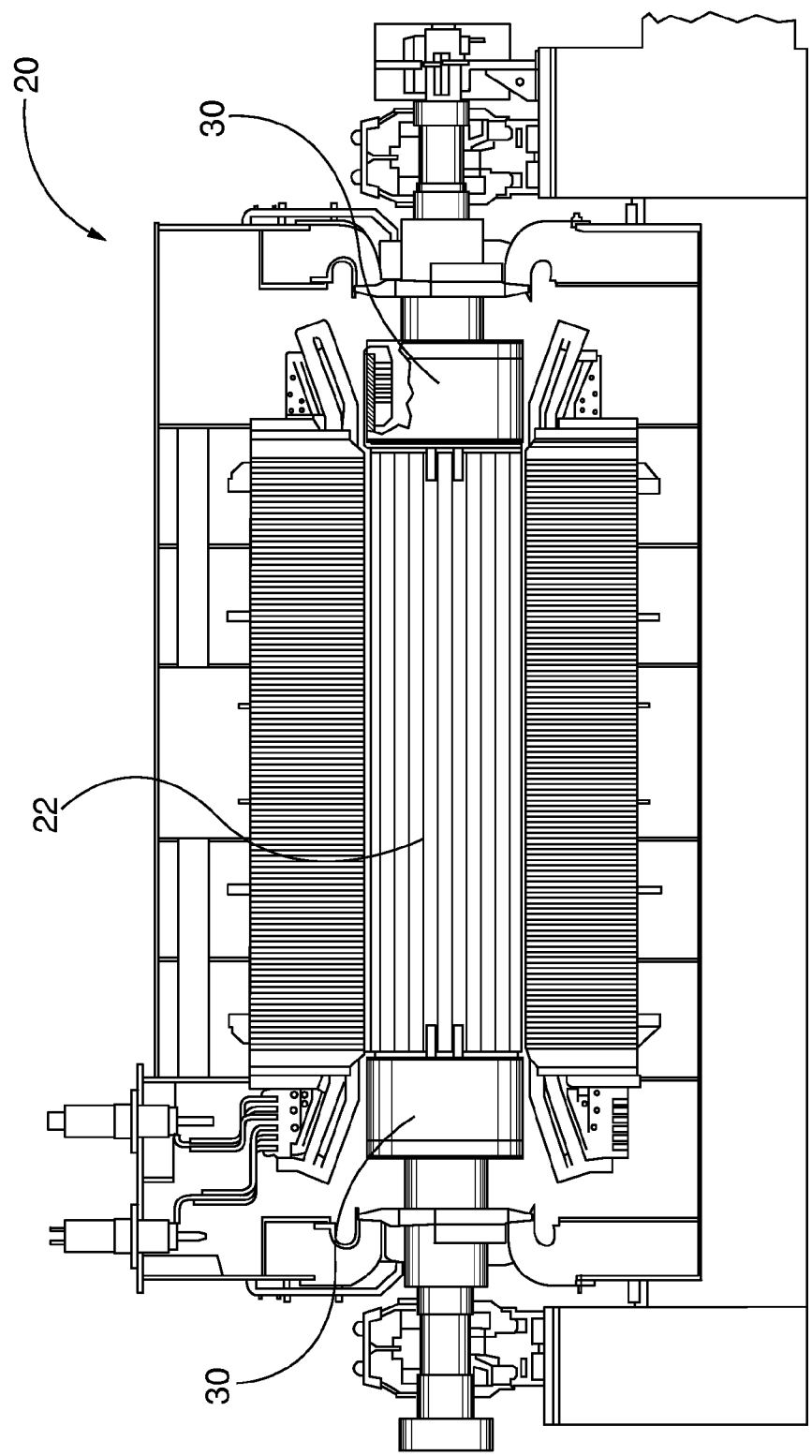
FIG. 1 is an axial cross-sectional view of a known generator, including.
Figure 2:
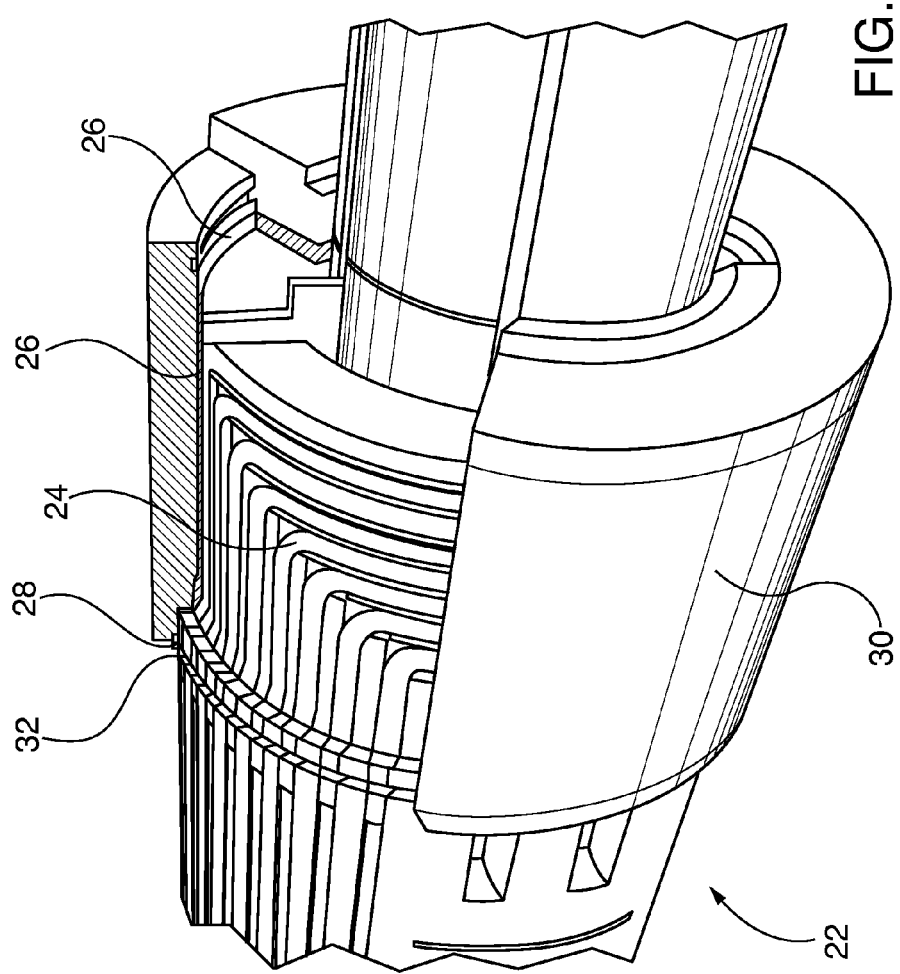
FIG. 2 is a perspective cut away view of a known retaining ring mounted on a known generator rotor.
Figure 3:
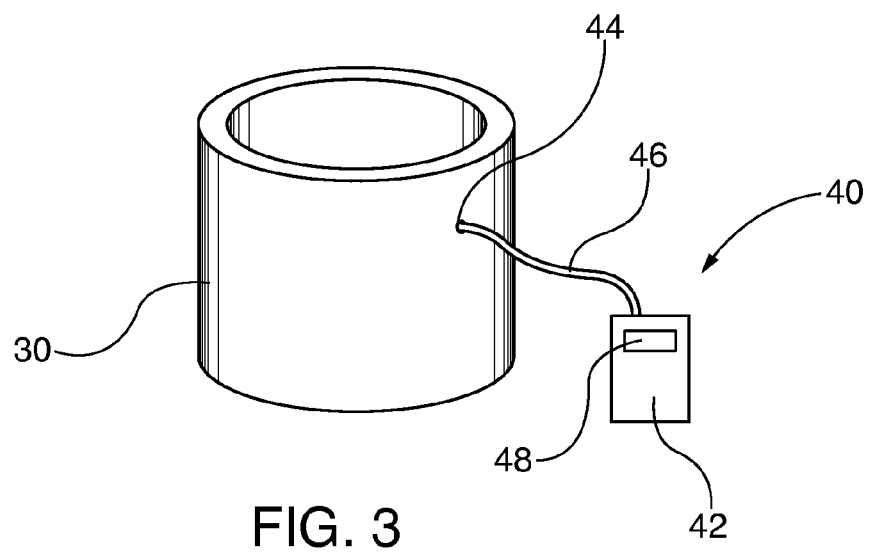
FIG. 3 is a schematic view of an exemplary eddy current test apparatus performing an eddy current test on a rotor retaining ring in accordance with an embodiment of the present invention.

After considering the following description, those skilled in the art will clearly realize that the teachings of the present invention can be readily utilized in eddy current non-destructive examination and evaluation of physical properties of a component, such as a generator retaining ring, rotor forging, rotor wedge, damper bar or other generator component, after experiencing potentially degrading thermal exposure during any stage of manufacture, assembly and service use. Referring to FIG. 3, eddy current testing is performed to determine whether the tested component, such as the generator retaining ring 30, is acceptable for service use, requires further modification (e.g., additional heat treatment processing) or whether is permanently unsuitable for service. Eddy current test measurements are correlated with component temperature exposure (e.g., absolute temperature and/or cumulative time-temperature heat absorption) and cumulative alteration of the component physical properties, such as, among others, material yield strength (YS), toughness, and tensile ductility. Using the eddy current test measurements and reference data correlating electrical conductivity with ring material thermal exposure, the component's physical properties are evaluated to determine its serviceability. The testing can be performed in situ in the field, such as for evaluation of generator rings within field serviced generators, without need to remove the component from its service environment during the testing procedure.

As shown in FIG. 3, exemplary tests are performed with known portable eddy current NDE inspection systems 40 commonly used for structural defect or anomaly testing without altering the tested component. An exemplary known eddy current inspection system is a SIGMATEST® 2.069 inspection system sold by Foerster Instruments Incorporated of Pittsburgh, Pa., USA. The known inspection system 40 has an analyzer 42, a test probe 44 that is in contact with the test object (here the retaining ring 30), a probe lead 46 that couples the probe to the analyzer 42, and a display 48 (or other known human machine interface or other readable interface) for displaying the electrical conductivity. Known eddy current meters often display electrical conductivity in reference to a percentage of the International Annealed Copper Standard (% IACS), wherein conductivity of other materials are stated as a percentage of copper conductivity ($58*10^6$ Siemens/meter at 20° C.).

Figure 4:
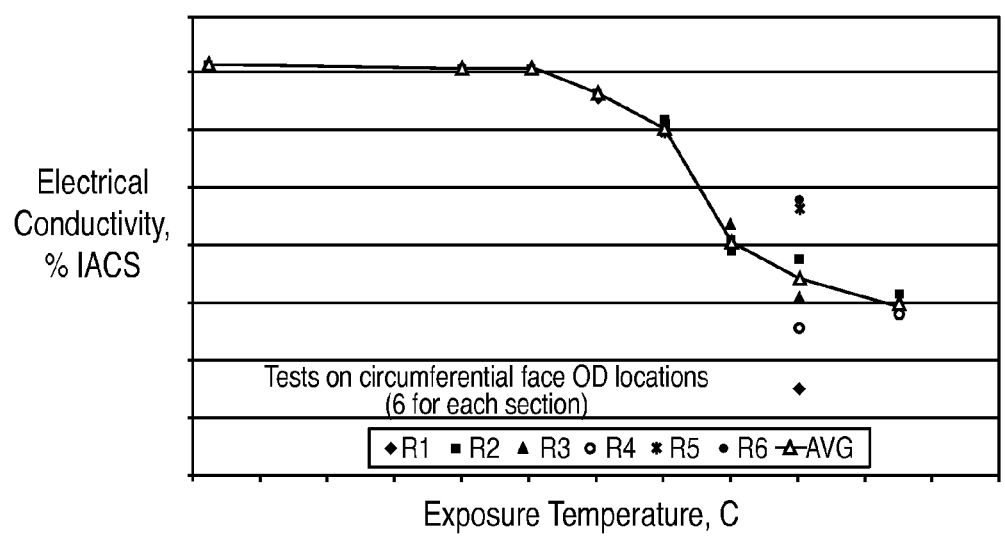
FIG. 4 is a graph of electrical conductivity measurements on a rotor retaining ring after one hour of temperature exposure at various temperatures.

Conductivity measurements shown in FIG. 4 were made at 6 locations on an outer diameter surface of plural samples of an exemplary generator retaining ring 30 constructed of 18Mn-18Cr austenic steel, using the aforementioned exemplary test instrument. The average value at each of the 6 measured locations is also shown in the figure. In the tests the plural ring samples were heated to temperatures from ambient temperature to more than 1000° C. for one hour exposure periods (i.e., each separate sample was heated to one designated temperature for one hour of heat exposure). Electrical conductivity was measured after ring cooling back to ambient temperature. It may be seen that there is no significant change in the eddy current values for samples exposed to lower temperatures, relative to the as-received material. A noticeable decrease is observed in the samples exposed to a critical temperature and higher. The values observed in each sample (except for the one) are also consistent with each other, showing little spread. One sample exposed to a high temperature exhibits more scatter in data than others did, but its difference compared to the ambient temperature baseline material is quite clear. All current measurements reported herein were made on the as-heat treated outer diameter ring surface without any further grinding. This was done to replicate shop-floor or field conditions, wherein such surface dressing of inspected, potentially overheated, rings may not always be feasible or desirable. Physical properties of the samples were also measured. Exposures above a critical temperature for the sampled 18Mn-18Cr austenic steel resulted in significant metallurgical changes (carbide and carbonitride precipitation, redissolution, and recrystallization).

It appears that the change in eddy current with thermal exposure is attributable to the nature and thickness of oxide film that forms on the sample surface. Changes in oxide film formation were observed at different temperature ranges and thermal exposure time periods.

With the NDE test methods of the present invention eddy current readings are used to identify degraded components in need of replacement without wasting additional service or manufacturing expense, but serviceable components are not unnecessarily scrapped. The current readings may be taken in the field with portable test apparatus while the tested component remains in situ, with good field repeatability. Eddy current testing is commonly used by test personnel to perform component defect evaluations, so no new extensive training is needed to perform the thermal degradation eddy current testing procedures. No physical alterations need to be made to the tested component.

Although various embodiments that incorporate the teachings of the present invention have been shown and described in detail herein, those skilled in the art can readily devise many other varied embodiments that still incorporate these teachings. The invention is not limited in its application to the exemplary embodiment details of construction and the arrangement of components set forth in the description or illustrated in the drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass direct and indirect mountings, connections, supports, and couplings. Further, "connected" and "coupled" are not restricted to physical or mechanical connections or couplings.

What is claimed is:

1. A method for non-destructive evaluation of one or more of yield strength, toughness, or tensile ductility physical properties of monolithic material forming a generator retaining ring, which property is altered by temperature change in the material that results from thermal exposure of the ring, comprising:
    providing a generator ring constructed of a monolithic, solid metal material;
    measuring the provided generator ring's International Annealed Copper Standard (IACS) electrical conductivity with an eddy current test system, at a single test frequency;
    obtaining reference data sets for test samples of the same monolithic, solid metal material, which are generated by:
        heating separate, plural, respective test samples, of the same monolithic material, to respective desired different temperatures for a common exposure period, and thereafter allowing each sample to cool to ambient temperature,
        measuring, for each respective cooled test sample, its IACS electrical conductivity, at the same single frequency, and one or more of its yield strength, toughness or tensile ductility physical properties;
    comparing the provided generator ring's measured IACS electrical conductivity to the reference data set's measured IACS conductivities of the test samples, and
    deriving, for the provided generator ring, one or more of its yield strength, toughness or tensile ductility physical properties or its prior thermal exposure temperature, based on its measured electrical conductivity and corresponding electrical conductivity/physical property information in the reference data set; and
    evaluating whether at least one of the provided generator ring's yield strength, toughness or tensile ductility physical properties, which is derived from the test data set, is acceptable for use in a generator.

2. The method of claim 1, the generator ring measuring performed while it is in situ within a generator.

3. The method of claim 2, the generator ring material selected from the group consisting of 18Mn18 Cr steel, 8Mn-8Cr-4Ni austenitic steel, 9Mn-6Cr-4Ni austenitic steel and 18Mn-5Cr austenitic steel.

4. The method of claim 1, the generator ring material selected from the group consisting of 18Mn18 Cr steel, 8Mn-8Cr-4Ni austenitic steel, 9Mn-6Cr-4Ni austenitic steel and 18Mn-5Cr austenitic steel.

5. The method of claim 1, the electrical conductivity measuring performed at multiple locations on the generator ring.

6. The method of claim 1, the generator ring measuring performed while it is in situ within a generator after shrink fit installation on a generator rotor.

7. A method for non-destructive evaluation of one or more of yield strength, toughness, or tensile ductility physical properties of monolithic material forming a generator component, which property is altered by temperature change in the material that results from thermal exposure of the component, comprising:
    providing a generator component constructed of a monolithic, solid metal material;
    measuring the provided component's International Annealed Copper Standard (IACS) electrical conductivity with an eddy current test system, at a single test frequency;
    obtaining reference data sets for test samples of the same monolithic, solid metal material, which are generated by:
        heating separate, plural, respective test samples, of the same monolithic material, to respective desired different temperatures for a common exposure period, and thereafter allowing each sample to cool to ambient temperature,
        measuring, for each respective cooled test sample, its IACS electrical conductivity, at the same single frequency, and one or more of its yield strength, toughness or tensile ductility physical properties;
    comparing the provided component's measured IACS electrical conductivity to the reference data set's measured IACS conductivities of the test samples, and
    deriving, for the provided component, one or more of its yield strength, toughness or tensile ductility physical properties or its prior thermal exposure temperature, based on its measured electrical conductivity and corresponding electrical conductivity/physical property information in the reference data set; and
    evaluating whether at least one of the provided component's yield strength, toughness or tensile ductility physical properties, which is derived from the test data set, is acceptable for use in a generator.

8. The method of claim 7, the component measuring performed while it is in situ without removal from its operative environment.

9. The method of claim 7, the component material selected from the group consisting of 18Mn18 Cr steel, 8Mn-8Cr-4Ni austenitic steel, 9Mn-6Cr-4Ni austenitic steel and 18Mn-5Cr austenitic steel.

10. The method of claim 7, the electrical conductivity measuring performed at multiple locations on the component.

11. A generator component whose physical properties use acceptability is evaluated using the method of claim 7.

12. The generator component of claim 11, comprising a generator retaining ring.

13. A generator comprising a generator retaining ring of claim 12.

* * * * *